United States Patent
Na et al.

(10) Patent No.: US 12,025,554 B2
(45) Date of Patent: Jul. 2, 2024

(54) METHOD FOR QUANTITATIVE ANALYSIS OF HYDROGEN IN POROUS SILICA

(71) Applicant: LG Chem, Ltd., Seoul (KR)

(72) Inventors: Sumin Na, Daejeon (KR); Jieun Kim, Daejeon (KR); Sunah Shin, Daejeon (KR); Min Hwan Jung, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1205 days.

(21) Appl. No.: 16/631,706

(22) PCT Filed: Jan. 16, 2019

(86) PCT No.: PCT/KR2019/000642
§ 371 (c)(1),
(2) Date: Jan. 16, 2020

(87) PCT Pub. No.: WO2019/143124
PCT Pub. Date: Jul. 25, 2019

(65) Prior Publication Data
US 2020/0166452 A1 May 28, 2020

(30) Foreign Application Priority Data
Jan. 19, 2018 (KR) .................. 10-2018-0006827

(51) Int. Cl.
*G01N 21/3504* (2014.01)
*C01B 33/12* (2006.01)
(Continued)

(52) U.S. Cl.
CPC ......... *G01N 21/3504* (2013.01); *C01B 33/12* (2013.01); *G01N 1/44* (2013.01);
(Continued)

(58) Field of Classification Search
CPC ............ G01N 21/3504; G01N 33/005; G01N 2001/4027; G01N 1/44; C01B 33/12
See application file for complete search history.

(56) References Cited

U.S. PATENT DOCUMENTS

| 4,798,704 A * | 1/1989 | Saito .................. B01L 7/00 422/549 |
| 2003/0082816 A1 | 5/2003 | Guerra |
| 2013/0337314 A1 | 12/2013 | Essaki et al. |

FOREIGN PATENT DOCUMENTS

| CN | 102539468 A | 7/2012 |
| CN | 104764695 A | 7/2015 |

(Continued)

OTHER PUBLICATIONS

US 9,991,035 B2, 06/2018, Hidaka et al. (withdrawn)
(Continued)

*Primary Examiner* — Lyle Alexander
*Assistant Examiner* — Mickey Huang
(74) *Attorney, Agent, or Firm* — Lerner David LLP

(57) ABSTRACT

A method for quantitative analysis of hydrogen gas generated due to the decomposition of Si—OH (silanol) in porous silica, which is a support of a metallocene catalyst is provided. The analysis enables the measurement of the content of hydrogen present in trace amounts in silica by employing an inert gas fusion-infrared absorption (IGFIA) method under specific pressure and temperature conditions.

5 Claims, 2 Drawing Sheets

(51) Int. Cl.
*G01N 1/40* (2006.01)
*G01N 1/44* (2006.01)
*G01N 33/00* (2006.01)

(52) U.S. Cl.
CPC ........ *G01N 33/005* (2013.01); *C01P 2004/61* (2013.01); *C01P 2006/12* (2013.01); *G01N 2001/4027* (2013.01)

(56) References Cited

FOREIGN PATENT DOCUMENTS

| CN | 103713106 B | 8/2016 |
|---|---|---|
| DE | 03001239 A1 | 7/1981 |
| JP | H06135759 A | 5/1994 |
| JP | H9257669 A | 10/1997 |
| JP | H10073579 A | 3/1998 |
| JP | 2003028852 A | 1/2003 |
| JP | 2003185579 A | 7/2003 |
| JP | 2005227045 A | 8/2005 |
| JP | 2008003050 A | 1/2008 |
| JP | 2008064460 A | 3/2008 |
| JP | 2011209191 A | 10/2011 |
| JP | 2014002890 A | 1/2014 |
| JP | 2014077648 A | 5/2014 |
| KR | 20050102154 A | 10/2005 |
| KR | 20090111513 A | 10/2009 |

OTHER PUBLICATIONS

Sheppard et al., Hydrogen adsorption on porous silica, 2008, International Journal of Hydrogen Energy 33 (2008) 1688-1692 (Year: 2008).*
Fink et al., Propene Polymerization with Silica-Supported Metallocene/MAO Catalysts, 1999, Chem. Rev. 2000, 100, 1377-1390 (Year: 1999).*
Orin Flanigan, Underground Gas Storage Facilities: Design and Implementation Chapter 4-Gas Law, 1995, Gulf Professional Publishing, p. 32-39 (Year: 1995).*
Search Report dated Jan. 26, 2022 from the Office Action for Chinese Application No. 201980003562.2 issued Feb. 8, 2022, 2 pages.
Anonymous, "836 Series—LECO Corporation", Jan. 2019, XP055725976, Retrieved from the Internet: URL:https://www.leco.com/product/836-series [retrieved on Aug. 28, 2020].
Extended European Search Report with Written Opinion for Application No. 19740688.7 dated Sep. 8, 2020, 11 pages.
Davis, et al., "Quantitative infrared spectroscopic measurement of hydroxyl concentrations in silica glass," Journal of Non-Crystalline Solids, Aug. 1, 1996, pp. 27-36, vol. 23.
International Search Report for Application No. PCT/KR2019/000642 dated May 3, 2019, 2 pages.
Nagasawa, et al., "FT-IR-ATR observation of SiOH and SiH in the oxide layer on a Si wafer," Microchimica Acta, Jan. 1, 1988, pp. 431-434, vol. 94.
Stingeder, et al., "Quantitative determination of oxygen in silicon by combination of FTIR-spectroscopy, inert gas fusion analysis and secondary ion mass spectroscopy," Fresenius Z Anal. Chem., Jan. 1989, pp. 576-582, vol. 333, Issue 4-5.

* cited by examiner

[Fig. 1]
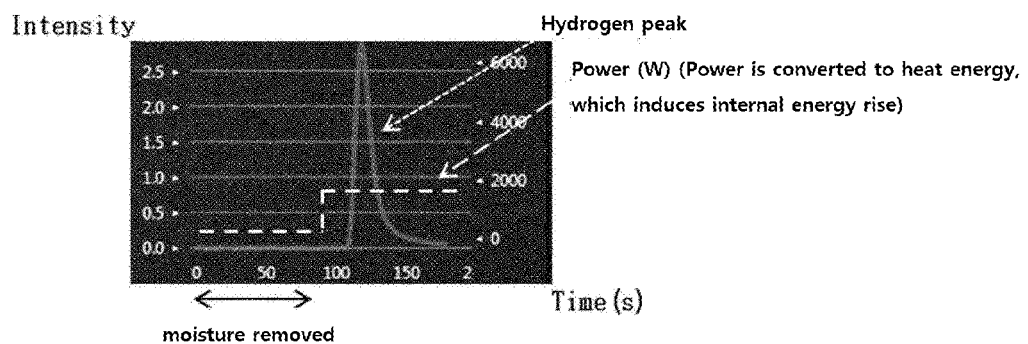
[Fig. 2]
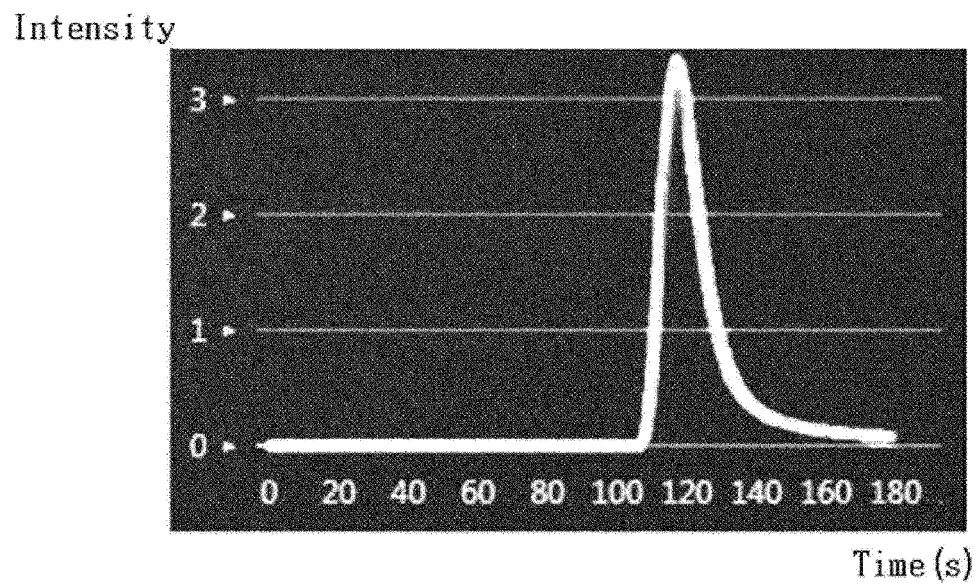

[Fig. 3]
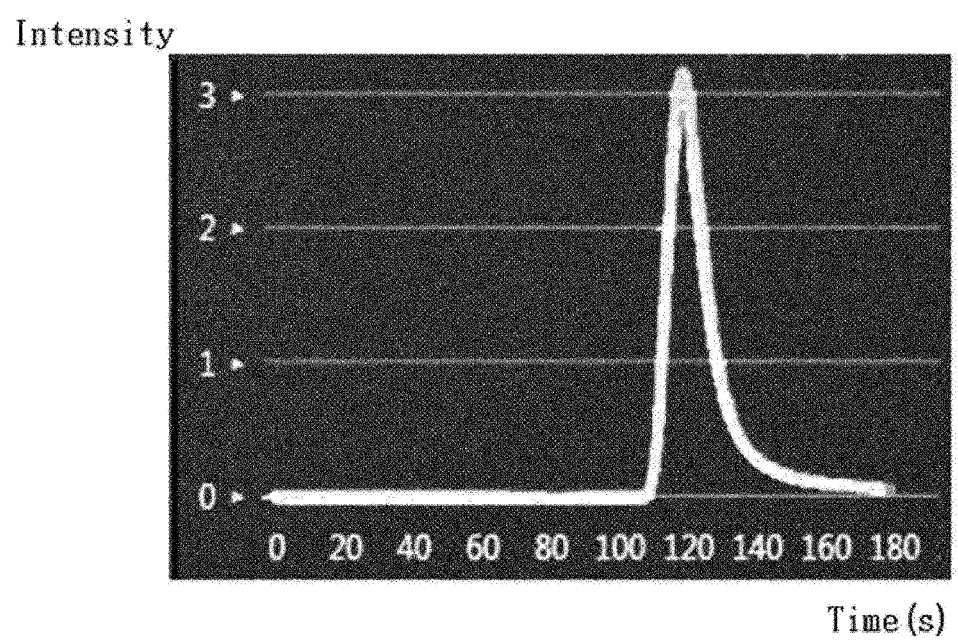

METHOD FOR QUANTITATIVE ANALYSIS OF HYDROGEN IN POROUS SILICA

BACKGROUND OF THE INVENTION

1. Cross-Reference to Related Applications

This application is a national phase entry under 35 U.S.C. § 371 of International Application No. PCT/KR2019/000642, filed Jan. 16, 2019, which claims priority to Korean Patent Application No. 10-2018-0006827, filed on Jan. 19, 2018, the entire disclosures of which are incorporated herein by reference.

2. FIELD OF THE INVENTION

The present invention relates to a method for quantitative analysis of hydrogen in porous silica used in the production of metallocene catalysts. More particularly, the present invention relates to a method for quantitatively analyzing hydrogen gas generated by decomposing Si—OH (silanol) in porous silica support of a metallocene catalyst.

3. Description of the Related Art

A metallocene catalyst, which is a useful catalyst for homopolymerization or copolymerization of olefin such as propylene, is characterized in that it is a coordination compound containing at least one substituted or unsubstituted cyclopentadienyl (Cp) group π-bonded to a transition metal. The metallocene catalyst may be a supported catalyst which is supported on an inorganic oxide such as talc, magnesia, titania or zirconia or a resinous support such as polyolefin. In the preparation of the supported metallocene catalyst, porous silica is widely used as a support, and the silica comprises a reaction site such as —OH, —O—MgCl, —O—$C_1$-$C_{10}$ alkyl, —O—$C_1$-$C_{10}$ alkylene-MgCl, or —O—$C_1$-$C_{10}$ alkylene-H on its surface. This reaction site means a site where the metallocene catalyst can be supported, and depending on the number thereof, the catalyst activity can be increased or the molecular weight distribution can be widened. In this connection, in order to confirm that the content of Si—OH in porous silica affects catalytic activity, there is a method of calculating the content of Si—OH by analyzing hydrogen content in the silica.

There are IR, XPS, and py-EGS/MS methods for analyzing hydrogen content in porous silica used in the production of metallocene catalysts. However, these methods have difficulties in analyzing hydrogen in a trace amount of 100 mg/kg to 1000 mg/kg. In addition, silica is vulnerable to moisture in the air. When silica is exposed to air, moisture is adsorbed on silica, making it difficult to separate moisture. The adsorbed moisture disturbs analysis of the content of hydrogen, and therefore the moisture is removed using heat and then the hydrogen content is analyzed. Accordingly, in the present invention, an attempt is made to remove moisture adsorbed on silica, decompose a Si—OH group in silica, resulting in hydrogen gas and to analyze the content of hydrogen using an inert gas fusion-infrared absorption (IGFIA) method. The IGFIA method is used for the analysis of H, O, and N in metals and minerals such as ceramics, and has improved detection limits.

SUMMARY OF THE INVENTION

It is an object of the present invention to provide a method for quantitatively analyzing hydrogen present in a trace amount in porous silica as a support used for preparing a metallocene catalyst.

According to the prior art, methods such as IR, XPS, and Py-EGS/MS, which are used to quantitatively analyze hydrogen in silica to calculate the content of Si—OH groups affecting activity of the silica supported metallocene catalyst, have a high detection limit, which makes it difficult to accurately analyze the content of hydrogen.

In order to overcome the above disadvantages, the present invention provides a method for analyzing the content of hydrogen gas in which moisture in silica is removed and a Si—OH group is decomposed, resulting in hydrogen gas, and then the hydrogen gas is transferred to an infrared detector (IR detector) using a carrier gas to analyze the content of hydrogen gas using an inert gas fusion-infrared absorption (IGFIA) method.

In one embodiment, the present invention provides a method for the quantitative analysis of hydrogen in porous silica, wherein the method comprises (i) heating porous silica used in the production of metallocene polypropylene catalyst at 0.1 to 0.15 bar and at 550 to less than 700° C., for example, 550 to 650° C. for 60 seconds to 1.5 minutes to evaporate moisture, and then adsorbing the evaporated moisture on a moisture scrubber to remove the adsorbed moisture, and (ii) heating the silica from which moisture has been removed at 0.1 to 0.15 bar and at 1200 to 1300° C. for 60 seconds to 1.5 minutes to decompose a Si—OH group, resulting in hydrogen gas, and then transferring the hydrogen gas to an infrared detector using a carrier gas to quantitatively analyze hydrogen using an inert gas fusion-infrared absorption (IGFIA) method.

That is, the present invention relates to a quantitative analysis of the content of hydrogen generated by removing moisture from porous silica and decomposing Si—OH groups using an IGFIA method.

In one embodiment, the heating step of (i) may be carried out at 0.102 to 0.104 bar and at 590 to 650° C. for 70 seconds to 1.2 minutes, such as at 0.1 bar and at 600 to 610° C. for 90 seconds.

In one embodiment, the heating step of (ii) may be carried out at 0.102 to 0.104 bar and at 1230 to 1260° C. for 70 seconds to 1.2 minutes, such as at 0.1 bar and at 1250° C. for 90 seconds. In the step (ii), the carrier gas may be helium (He) gas.

In one embodiment, the porous silica has an average particle size of 25 to 60 μm and a BET surface area of 300 to 350 m²/g.

In one embodiment, the hydrogen gas analyzer used in the IGFIA method of the present invention is not particularly limited as long as it is commonly used in the art, and may be, for example, ONH836 (LECO Corporation).

In one embodiment, the infrared detector used in the present invention is not particularly limited as long as it is commonly used in the art, and may be, for example, ONH836 (LECO Corporation).

Effect of the Invention

In the conventional method, it is difficult to analyze the exact content of hydrogen present in a trace amount in the porous silica used as a support of the metallocene catalyst because of high detection limit. However, according to the present invention, a trace amount of hydrogen can be analyzed by quantitatively analyzing the hydrogen gas generated by decomposing Si—OH in the silica under specific pressure and temperature conditions using an IGFIA method.

BRIEF DESCRIPTION OF THE DRAWINGS

FIG. 1 shows the measurement of hydrogen content after removing moisture in the silica and decomposing Si—OH according to one embodiment of the present invention.

FIG. 2 shows the hydrogen content in the silica analyzed according to Example 1 of the present invention.

FIG. 3 shows the hydrogen content in the silica analyzed according to Example 2 of the present invention.

DETAILED DESCRIPTION OF THE INVENTION

Hereinafter, embodiments of the present invention will be described in more detail.

The terms and words used in the present specification and claims should not be construed as limited to ordinary or dictionary meanings and should be construed as meaning and concept consistent with the technical idea of the present invention based on the principle that the inventor can properly define the concept of the term in order to explain its invention in the best way possible.

It is an object of the present invention to provide a method for quantitatively analyzing the content of hydrogen present in trace amounts in porous silica as a support used in the production of metallocene catalysts.

In order to achieve the object, in the method of the present invention, moisture in silica is removed and then a Si—OH group is decomposed, resulting in hydrogen gas, and the hydrogen gas is transferred to an infrared detector (IR detector) using a carrier gas to analyze the content of hydrogen gas by an inert gas fusion-infrared absorption (IGFIA) method.

In one embodiment, the present invention provides a method for the quantitative analysis of hydrogen in porous silica, wherein the method comprises (i) heating porous silica used in the production of metallocene polypropylene catalyst at 0.1 to 0.15 bar and at 550 to less than 700° C., for example, 550 to 650° C. for 60 seconds to 1.5 minutes to evaporate moisture, and then adsorbing the evaporated moisture on a moisture scrubber to remove the adsorbed moisture, and (ii) heating the silica from which moisture has been removed at 0.1 to 0.15 bar and at 1200 to 1300° C. for 60 seconds to 1.5 minutes to decompose a Si—OH group, resulting in hydrogen gas, and then transferring the hydrogen gas to an infrared detector using a helium (He) carrier gas to quantitatively analyze hydrogen using an inert gas fusion-infrared absorption (IGFIA) method.

In the present invention, the moisture scrubber absorbs moisture generated by heating of the porous silica sample and removes water vapor as shown in the following reaction scheme:

$$Mg(ClO_4)_2(s)+3H_2O(g) \rightarrow 2HClO_4 \cdot 2H_2O(s)+MgO(s)$$

The moisture scrubber may be made of $Mg(ClO_4)_2(s)$, for example and $Mg(ClO_4)_2(s)$ exists in a crystalline form before it absorbs moisture, but when it absorbs moisture it turns into a soft powder form.

The pressure, temperature, and time range defined in the heating step of (i) correspond to optimum conditions in which the moisture in the porous silica sample is evaporated and the evaporated water vapor is adsorbed on the moisture scrubber. If the pressure, temperature and time range are out of the above-defined range, the analysis accuracy of the hydrogen content in the silica sample may be degraded.

With respect to the temperature in the heating step of (i), the content of evaporated moisture was measured by heating the silica at the respective temperatures shown in the table below in an analytical environment of 0.1 bar. The measurement results are as follows:

| Temperature (° C.) | Moisture content (wt %) |
|---|---|
| 700 | 0.02 |
| 850 | 14.5 |
| 1100 | 16.4 |
| 1250 | 63.7 |
| 1500 | 80.7 |
| 1750 | 84.5 |
| 1850 | 89.1 |
| 2100 | 98.9 |
| 2200 | 95.5 |
| 2300 | 95.5 |

As a result of measurement, moisture in the vapor form evaporated from silica was not measured below 700° C. Thus, below 700° C., all water vapor evaporated from the silica can be removed. However, at a temperature of 700° C. or higher, evaporated water vapor exists and some of the water vapor is decomposed into hydrogen and oxygen, so that the hydrogen content in the silica can not be accurately analyzed.

The upper and lower limits of the pressure range of the heating step of (i) are set in consideration of the operating conditions of an apparatus used in the IGFIA method of the present invention, for example, ONH836 (LECO Corporation).

In addition, the upper and lower limits of the time range of the heating step of (i) are set in consideration of the time taken for moisture to sufficiently evaporate from the silica and to adsorb on the moisture scrubber.

In one embodiment, the heating step of (i) may be carried out at 0.102 to 0.104 bar and at 590 to 650° C. for 70 seconds to 1.2 minutes.

In other embodiment, the heating step of (i) may be carried out at 0.1 bar and at 600 to 610° C. for 90 seconds.

The pressure, temperature and time range defined in the heating step (ii) corresponds to the optimum conditions for decomposing SiOH in silica to generate hydrogen gas.

If the temperature range of the heating step of (ii) is out of the above range, the SiOH in the silica is not sufficiently decomposed.

In one embodiment, the heating step of (ii) may be carried out at 0.102 to 0.104 bar and at 1230 to 1260° C. for 70 seconds to 1.2 minutes.

In other embodiment, the heating step of (ii) may be carried out at 0.1 bar and at 1250° C. for 90 seconds.

In one embodiment, the porous silica has an average particle size of 25 to 60 μm, for example 30 to 55 μm and a BET surface area of 300 to 350 m²/g, for example 320 m²/g.

The IGFIA method used in the present invention is a method in which a small amount of a sample is placed in a graphite crucible in a furnace and burned at a high temperature under a stream of Ar or He as an inert carrier gas, for example by first heating at 600° C., then second heating to 1250° C., and the released gas is measured by infrared absorption. It is known to release $H_2$ by burning at high temperature and analyze the released $H_2$ by an infrared detector.

In one embodiment, the hydrogen gas analyzer used in the IGFIA method of the present invention is not particularly limited as long as it is commonly used in the art, and may be, for example, ONH836 (LECO Corporation).

In one embodiment, the infrared detector used in the present invention is not particularly limited as long as it is commonly used in the art, and may be, for example, ONH836 (LECO Corporation).

Hereinafter, embodiments of the present invention will be described in detail so that those skilled in the art can easily carry out the present invention. The present invention may, however, be embodied in many different forms and should not be construed as limited to the embodiments set forth herein.

EXAMPLES

1. Preparation of Sample and Analysis of Hydrogen Content (1) A silica sample A (Example 1) having an average particle size of 31 μm and a silica sample B (Example 2) having an average particle size of 55 μm (Grace, SYLOPOL948) were put into a Sn capsule (LECO Corporation, tin capsule, ID 5.0 mm, height 13 mm)/Ni basket (LECO, Ni basket, 1 g) in an amount of 0.01 g, respectively.

(2) A double graphite capsule (graphite crucible, LECO Corporation) was installed in a furnace (ONH836, LECO Corporation) and a Sn capsule/Ni basket containing the sample from (1) above was placed therein.

(3) Using He carrier gas, the sample from (2) above was heated at 600° C. and 0.1 bar for 90 seconds to evaporate moisture and the evaporated moisture was removed by adsorption on a moisture scrubber made of $Mg(ClO_4)_2$ [heating step 1].

(4) Next, the sample from (3) above was decomposed by heating at 0.1 bar and at 1250° C. for 90 seconds, and the resulting hydrogen gas was measured using an ND-IR detector (heating step 2).

The results of measurement of hydrogen content after removing moisture in a silica sample and decomposing Si—OH according to the present example are shown in FIG. 1.

2. Analysis of Hydrogen Content

The results of hydrogen content analysis of the silica sample A having an average particle size of 31 μm and the silica sample B having an average particle size of 55 μm mentioned in "1. Preparation of sample and analysis of hydrogen content" are shown in the table below. As the particle size increases, the relative surface area decreases. From this, the amount of OH adsorbed on the silica surface can be expected to be small. Relative standard deviation in the following table is data for determining the reproducibility of the analysis, so it is not related to the silica particle size.

|  | Average particle size (μm) | Hydrogen content (mg/kg) | Relative standard deviation (RSD %) |
|---|---|---|---|
| Silica A (Example 1) | 31 | 598 | 2.12 |
| Silica B (Example 2) | 55 | 445 | 5.71 |

The analysis results of hydrogen content for the silica A (Example 1) and the silica B (Example 2) based on the above table are shown in FIGS. 2 and 3, respectively. As can be seen from the above table, according to the quantitative method of the present invention, it is possible to quantitatively analyze hydrogen present in a trace amount of 100 mg/kg to 1000 mg/kg in silica.

It will be understood by those skilled in the art that various changes in form and details may be made therein without departing from the spirit or essential characteristics of the invention. Therefore, it should be understood that the above-described embodiments are illustrative in all aspects and not restrictive. In addition, the scope of the present invention is indicated by the following claims rather than the above detailed description.

What is claimed is:

1. A method for quantitative analysis of hydrogen in porous silica, comprising:
   (i) heating porous silica used in a production of metallocene polypropylene catalyst at 0.1 bars to 0.15 bars and at 550° C. to less than 700° C. for 60 seconds to 1.5 minutes to evaporate moisture, and then adsorbing the evaporated moisture on a moisture scrubber to remove the adsorbed moisture, and
   (ii) heating the porous silica from which moisture has been removed at 0.1 bar to 0.15 bars and at 1200° C. to 1300° C. for 60 seconds to 1.5 minutes to decompose a Si—OH group, resulting in hydrogen gas, and then transferring the hydrogen gas to an infrared detector using a carrier gas to quantitatively analyze hydrogen using an inert gas fusion-infrared absorption (IGFIA) method
   wherein the porous silica has an average particle size of 30 μm to 55 μm and a BET surface area of 300 $m^2/g$ to 350 $m^2/g$,
   wherein the porous silica includes hydrogen in an amount ranging from 100 mg/kg to 1000 mg/kg.

2. The method according to claim 1, wherein (1) the heating is carried out at 0.102 bars to 0.104 bars and at 590° C. to 650° C. for 70 seconds to 1.2 minutes.

3. The method according to claim 1, wherein (1) the heating is carried out at 0.1 bars and at 600° C. to 610° C. for 90 seconds.

4. The method according to claim 1, wherein (ii) the heating is carried out at 0.102 bars to 0.104 bars and at 1230° C. to 1260° C. for 70 seconds to 1.2 minutes and wherein the carrier gas is helium (He) gas.

5. The method according to claim 1, wherein (ii) the heating is carried out at 0.1 bars and at 1250° C. for 90 seconds.

* * * * *